(12) United States Patent
Bongartz et al.

(10) Patent No.: US 9,303,046 B2
(45) Date of Patent: Apr. 5, 2016

(54) PROCESS FOR THE PREPARATION OF HETEROCYCLIC ESTER DERIVATIVES

(71) Applicant: Janssen Pharmaceutica NV, Beerse (BE)

(72) Inventors: Jean-Pierre André Marc Bongartz, Turnhout (BE); Alfred Elisabeth Stappers, Oud-Turnhout (BE); Christopher A. Teleha, Fort Washington, PA (US); Koen Johan Herman Weerts, Vosselaar (BE); Kenneth J. Wilson, Playas Del Coco (CR)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/959,120

(22) Filed: Aug. 5, 2013

(65) Prior Publication Data

US 2014/0046072 A1     Feb. 13, 2014

Related U.S. Application Data

(60) Provisional application No. 61/680,412, filed on Aug. 7, 2012.

(51) Int. Cl.
*C07F 7/10* (2006.01)
*C07F 7/08* (2006.01)

(52) U.S. Cl.
CPC ............... *C07F 7/0812* (2013.01); *C07F 7/083* (2013.01); *C07F 7/10* (2013.01)

(58) Field of Classification Search
CPC .................... C07D 233/90; C07F 7/0812
See application file for complete search history.

(56) References Cited

U.S. PATENT DOCUMENTS

| | | | |
|---|---|---|---|
| 2,466,420 A | 4/1949 | Hagemeyer et al. | |
| 3,226,394 A | 12/1965 | Schipper | |
| 4,551,540 A | 11/1985 | Hechenbleikner et al. | |
| 5,190,541 A | 3/1993 | Abele et al. | |
| 5,474,765 A | 12/1995 | Thorpe | |
| 5,762,918 A | 6/1998 | Thorpe | |
| 5,855,866 A | 1/1999 | Thorpe et al. | |
| 5,874,442 A | 2/1999 | Doll et al. | |
| 5,944,718 A | 8/1999 | Austin et al. | |
| 5,968,952 A | 10/1999 | Venet et al. | |
| 6,037,350 A | 3/2000 | Venet et al. | |
| 6,100,254 A | 8/2000 | Budde et al. | |
| 6,117,432 A | 9/2000 | Ganne et al. | |
| 6,169,096 B1 | 1/2001 | Venet et al. | |
| 6,187,786 B1 | 2/2001 | Venet et al. | |
| 6,235,746 B1 | 5/2001 | Davis et al. | |
| 6,342,219 B1 | 1/2002 | Thorpe et al. | |
| 6,346,625 B1 | 2/2002 | Karabelas et al. | |
| 6,383,790 B1 | 5/2002 | Shokat | |
| 6,420,387 B1 | 7/2002 | Venet et al. | |
| 6,458,800 B1 | 10/2002 | Angibaud et al. | |
| 6,596,746 B1 | 7/2003 | Das et al. | |
| 6,692,491 B1 | 2/2004 | Phan | |
| 6,958,243 B2 * | 10/2005 | Larhed et al. | ......... 436/128 |
| 7,157,456 B2 | 1/2007 | Straub et al. | |
| 7,208,493 B2 | 4/2007 | Wrasidlo et al. | |
| 7,427,683 B2 | 9/2008 | Player et al. | |
| 7,429,603 B2 | 9/2008 | Player et al. | |
| 7,645,755 B2 | 1/2010 | Illig et al. | |
| 7,662,837 B2 | 2/2010 | Illig et al. | |
| 7,790,724 B2 | 9/2010 | Player et al. | |
| 7,795,279 B2 | 9/2010 | Ballentine et al. | |
| 7,973,035 B2 | 7/2011 | Illig et al. | |
| 2002/0016625 A1 | 2/2002 | Falotico et al. | |
| 2002/0019414 A1 | 2/2002 | Altmann et al. | |
| 2003/0153610 A1 | 8/2003 | Straub et al. | |
| 2004/0049032 A1 | 3/2004 | Charrier et al. | |
| 2005/0113566 A1 | 5/2005 | Player et al. | |
| 2005/0131022 A1 * | 6/2005 | Player et al. | ......... 514/318 |
| 2006/0040995 A1 | 2/2006 | Bacque et al. | |
| 2006/0100619 A1 | 5/2006 | McClurken et al. | |
| 2006/0122181 A1 | 6/2006 | Ikemoto et al. | |
| 2006/0189623 A1 | 8/2006 | Illig et al. | |
| 2006/0258724 A1 | 11/2006 | Straub et al. | |
| 2006/0281788 A1 | 12/2006 | Baumann et al. | |

(Continued)

FOREIGN PATENT DOCUMENTS

EP     1566379    8/2005
GB     1189719    4/1970

(Continued)

OTHER PUBLICATIONS

Brennfuhrer et al. Angew. Chem. Int. Ed. 2009, 48, 4114-4133.*
Martinelli et al. J. Org. Chem. 2008, 73, 7102-7107 and its supporting information.*
Magerlein et al Journal of Molecular Catalysis A, 2000, 156, 213-221.*
Abarbri et al., J. Org. Chem. (2000), 65, 4618-4634.
Barkenbus et al., Journal of Organic Chemistry (1951), 16, 232-8.
Brown et al., J. Chem. Soc., Perkin Trans. 2, 1039-1051 (2002).
Byrn et al., Solid-State Chemistry of Drugs, Second Edition, 1999, pp. 233-247.
Crandall et al., J. Am. Chem. Soc. (1968), 90, 6251-6253.
Eastwood, P., Tetrahedron Lett. (2000), 41, 3705-8.
Gavezzotti, "Are Crystal Structures Predictable?" Accounts of Chemical Research, vol. 27, pp. 309-314 (1994).
Guillory (in Brittain ed.) Polymorphism, etc., NY: Marcel Dekker, Inc., 1999, 1-2, 183-226.
Harmata et al., Org. Lett. (2000), 2, 2703-2705.
Hess et al., J. Am. Chem. Soc. (1998), 120, 12310.

(Continued)

*Primary Examiner* — Matthew Coughlin

(57) ABSTRACT

The present invention is directed to a process for the preparation of heterocyclic ester derivatives of formula I

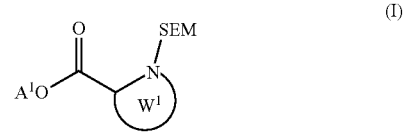

(I)

wherein $A^1$, SEM, and $W^1$ are as defined herein. Such compounds are useful as intermediates in the synthesis of derivatives useful as protein tyrosine kinase inhibitors, more particularly inhibitors of c-fms kinase.

6 Claims, No Drawings

(56) References Cited

U.S. PATENT DOCUMENTS

| | | |
|---|---|---|
| 2007/0249593 A1 | 10/2007 | Illig et al. |
| 2007/0249608 A1 | 10/2007 | Illig et al. |
| 2007/0249649 A1 | 10/2007 | Illig et al. |
| 2008/0051402 A1 | 2/2008 | Illig et al. |
| 2009/0105296 A1 | 4/2009 | Illig et al. |
| 2009/0197913 A1 | 8/2009 | Baumann et al. |
| 2011/0195960 A1 | 8/2011 | Illig et al. |

FOREIGN PATENT DOCUMENTS

| | | |
|---|---|---|
| WO | WO 94/10138 | 5/1994 |
| WO | WO 96/11932 | 4/1996 |
| WO | WO 96/21452 | 7/1996 |
| WO | WO 96/32907 | 10/1996 |
| WO | WO 97/16443 | 5/1997 |
| WO | WO 97/21701 | 6/1997 |
| WO | WO 97/30992 | 8/1997 |
| WO | WO 98/06700 | 2/1998 |
| WO | WO 98/28264 | 7/1998 |
| WO | WO 98/28303 | 7/1998 |
| WO | WO 98/40383 | 9/1998 |
| WO | WO 98/49157 | 11/1998 |
| WO | WO 98/54174 | 12/1998 |
| WO | WO 99/45712 | 9/1999 |
| WO | WO 99/45912 | 9/1999 |
| WO | WO 00/01691 | 1/2000 |
| WO | WO 00/02871 | 1/2000 |
| WO | WO 00/12498 | 3/2000 |
| WO | WO 00/12499 | 3/2000 |
| WO | WO 00/27820 | 5/2000 |
| WO | WO 02/68406 | 5/2000 |
| WO | WO 00/39082 | 7/2000 |
| WO | WO 01/47897 | 7/2001 |
| WO | WO 01/47919 | 7/2001 |
| WO | WO 01/49667 | 7/2001 |
| WO | WO 02/32861 A2 | 4/2002 |
| WO | WO 02/092599 A1 | 11/2002 |
| WO | WO 03/024931 A1 | 3/2003 |
| WO | WO 03/024969 A1 | 3/2003 |
| WO | WO 03/035009 A2 | 5/2003 |
| WO | WO 03/037347 A1 | 5/2003 |
| WO | WO 03/057690 A1 | 7/2003 |
| WO | WO 03/099771 A2 | 12/2003 |
| WO | WO 03/099796 | 12/2003 |
| WO | WO 2004/005281 A1 | 1/2004 |
| WO | WO 2004/016597 A2 | 2/2004 |
| WO | WO 2004/018419 A2 | 3/2004 |
| WO | WO 2004/022525 | 3/2004 |
| WO | WO 2004/039782 A1 | 5/2004 |
| WO | WO 2004/043389 A2 | 5/2004 |
| WO | WO 2004/046120 A2 | 6/2004 |
| WO | WO 2004/058749 A1 | 7/2004 |
| WO | WO 2004/085388 | 10/2004 |
| WO | WO 2004/096795 | 11/2004 |
| WO | WO 2005/012220 | 2/2005 |
| WO | WO 2005/040139 | 5/2005 |
| WO | WO 2005/047273 | 5/2005 |
| WO | WO 2005/073225 | 8/2005 |
| WO | WO 2006/047277 | 5/2006 |
| WO | WO 2006/047504 | 5/2006 |
| WO | WO 2006/135630 | 12/2006 |
| WO | WO 2006/135636 | 12/2006 |
| WO | WO 2006/135713 | 12/2006 |
| WO | WO 2006/135718 | 12/2006 |
| WO | WO 2006/138155 A1 | 12/2006 |
| WO | WO 2007/048088 | 4/2007 |
| WO | WO 2009/058968 | 5/2009 |

OTHER PUBLICATIONS

Hogermeier et al., Chem. Eur. J., 2007, 13, 2410.
Johnson et al., J. Org. Chem. (1970), 35(3), 584-592.
Kim et al., European Journal of Organic Chemistry (2000), 12, 2195-2201.
Larock, R.C., Comprehensive Organic Transformations, 2$^{nd}$ Ed., Wiley-VCH, NY, (1999), pp. 996-1003.
Lee, K. and Cha, J. K., J. Amer. Chem. Soc., 123: 5590-5591 (2001).
Lipshutz et al., Tetrahedron Lett. (1988), 29, 3411-3414.
McBee et al., Journal of the American Chemical Society (1957), 79, 2323-5.
Meltzer et al., Bioorganic & Medicinal Chemistry (2002), 10(11) and 3583-3591.
Noyori et al., Org. React., 1983, 29, 163.
Regan et al., J. Med. Chem., 46: 4676-86 (2003).
Reinecke et al., Chemistry-A European Journal (1995), 1(6), 368-73.
Sasaki et al., Tett. Lett. (1982), 23, 1693.
Sato et al., Bulletin of the Chemical Society of Japan (1983), 56(9), 2680-99.
Sato et al., Bulletin of the Chemical Society of Japan (1984), 57(9), 2515-25.
Schmid et al., Helv. Chim. Acta. (1974), 57, 1883 [see English summary provided].
Sendelbach, et al, Journal of Organic Chemistry (1999), 64(10), 3398-3408.
Stille, J. K., Angew. Chem, Int. Ed. Engl., 25: 508-524 (1986).
Sundermeier, U., Doebler, C. and Beller, M., Modern Oxidation Methods, Baeckvall, J. (Ed.)., 1-20, Wiley-Verlag (2004) Weinheim, Germany (2004).
Takahashi, K., et al, Chem. Lett. (2000), 126-7.
Takaya et al., J Amer Chem Soc, (1978), 100(6), 1765-77.
West et al., J. Org. Chem (1993), 58, 6795-6803.
Wroblewski et al., Journal of the American Chemical Society (1996), 118, 10168-10174.
Abdel-Magid et al, "Reductive Amination of Aldehydes and Ketones with Sodium Triacetoxyborohydride.Studies on Direct and Indirect Reductive Amination Procedures", J Org. Chem., vol. 61 pp. 3849-3862 (1996).
Aboutaleb et al., International Sem in Surgical Oncol 6(17): 1-3, 2006.
Acute myeloid leukemia: MedlinePlus Medical Encyclopedia. Retrieved on Dec. 28, 2010. Electronic Resource: http://www.nlm.nih.gov/medlineplus/ency/article/000542.htm].
Advani, A., Curr Hematologic Malignancy Reports 1:101-107,2006.
Ansari-Lari, A. et al., "FLT3 mutations in myeloid sarcoma" British Journal of Haematology. Sep. 2004 126(6):785-91.
Armstrong, S.A. et al., (2004) "FLT3 mutations in childhood acute lymphoblastic leukemia." Blood. 103: 3544-6.
Arnon et al., "Monoclonal Antibodies for Immunotargeting of Drugs in Cancer Therapy", in Monoclonal Antibodies and Cancer Therapy, Reisfeld et al. (eds.), pp. 243-256 (Alan R. Liss, Inc. 1985).
Auewarakul et al., Ann Hematol, 85:108-112, 2006.
Baumann CA, Zeng L, Donatelli RR, Maroney AC. Development of a quantitative, high-throughput cell-based enzyme-linked immunosorbent assay for detection of colony-stimulating factor-1 receptor tyrosine kinase inhibitors. J Biochem Biophys Methods. 2004; 60:69-79.
Beller et al., Applied Homogeneous Catalysis with Organometallic Compounds, Cornils, B. and Herrmann, W. A. (Eds.), 2, 1009-1024, VCH, Weinheim, Germany (1996).
Berenbaum et al. What is synergy? Pharmacological Reviews, 1989.
Berge, S., et al, "Pharmaceutical Salts", J. Pharm. Sci., 1977, Jan, 66(1): 1-19.
Bodansky, M. et al., "The Practice of Peptide Synthesis", Springer-Verlag, NY (1984).
British Journal of Haematology, "Flt3 mutations and leukaemia", 2003,122(4):523-38.
Buchner T., W. Hiddemann, et al. (2002). "Acute myeloid leukemia: treatment over 60." Rev Clin Exp Hematol. 6(1):46-59.
Buchwald, E.L. et al., Top. Curr. Chem., 219:131-209 (2001).
Burnett, A. K. (2002). "Acute myeloid leukemia: treatment of adults under 60 years." Rev Clin Exp Hematol 6(1): 26-45.
Canibano, V. et al., Synthesis 14, 2175 (2001).
ChemBlink. Tipifarnib. Electronic Resource. Retrived on Dec. 18, 2010: [http://www.chemblink.com/products/192185-72-1.htm].
Chou TC, Talalay P. (1984) "Quantitative analysis of dose-effect relationships: the combined effects of multiple drugs or enzyme inhibitors." Adv Enzyme Regul. 22:27-55.
Coll. Czech. Chem. Commun.: 31(11), 4432-41, (1966), Palecek, J.

(56) References Cited

OTHER PUBLICATIONS

Comprehensive Organic Transformations: Larock, R.S.; Wiley and Sons Inc., USA 1999.

Cortes. Farnesyltransferase inhibitors in acute myeloid leukemia and myelodysplastic syndromes. Clinical Lymphoma, vol. 4, Suppl. 1, S30-S35, 2003.

Cummins et al., Tetrahedron (1988), 44(16), 5151.

Drexler, H. G. et al. (2004), "FLT3: receptor and ligand"; Growth Factors 22(2):71-3.

Drexler, H.G., "The Leukemia-Lymphoma Cell Line Factsbook", Academic Pres:SanDiego, CA, 2000.

Ferrara et al., "Prognostic factors and therapeutic options for relapsed or refractory acute myeloid leukemia." Haematologica. Aug. 2004, vol. 89, No. 8, Aug. 2004; pp. 998-1008.

Gilliand, G., et.al, "The roles of FLT3 in mematopoiesis and leukemia", Blood. 2002; 100:1532-42.

Gotlib, J (2005) "Farnesyltransferase inhibitor therapy in acute myelogenous leukemia." Curr. Hematol. Rep.;4(1):77-84.

Gould, P., "Salt selection for basic drugs", Ref. International J. Pharm. 1986, 33, 201-217.

Gray, M. et al., Tetrahedron Lett., 41:6237-40 (2000).

Griswold, I. J. et al., "Effects of MLN518, A Dual FLT3 and KIT inhibitor, on Normal and Malignant Hematopoiesis" Blood, Jul. 2004 [Epub ahead of print].

Haluska P., G.K. Dy, A.A. Adjei. (2002) "Farnesyl transferase inhibitors as anticancer agents." Eur J Cancer. 38(13):1685-700.

Han, J., Advances in Characterization of Pharmaceutical Hydrates, Trends in Bio/PharmaceuticalIndustry, pp. 25-29. Mar. 2006.

Hartwig, J.F., "Organopalladium Chemistry for Organic Synthesis," Wiley Interscience, NY (2002).

Hellstrom et al., "Antibodies for Drug Delivery", in Controlled Drug Delivery (2nd Ed.), Robinson et al. (eds.), pp. 623-653 (Marcel Dekker, Inc. 1987).

Hengartner, MO. (2000) "The biochemistry of apoptosis." Nature 407:770-76.

Hill et al., J. Am. Chem. Soc. (1973), 95, 1338.

Iddon. B. et al., J. Chem. Soc. Perkin Trans. 1., 1370, (1980).

Ishikubo et al (Jpn J Clin Oncol 36:494-498, 2006).

Johnson et al., Brit J Cancer, 84:1424-1431 (2001).

Lyon et al., J. Med. Chem., 29: 630-634 (1986).

Romeo et al., J. Med. Chem., 46: 2877 (2003).

Kamwakami J., et al. "A Convenient Synthesis of 4(5)-Alkylacyl-1H-imidazoles from 4(5)-Imidazolecarboxaldehyde" Synthesis, No. 5, pp. 677-680 (2003).

Katritsky, A. et al., "para-Formylation of Nitroarenes via Vicarious Nucleophilic Substitution of Hydrogen with Tris(benzotriazol-1-yl)methane", Tetrahedron Lett., 37:347-50 (1996).

Kolder, C.R., et al, "Synthesis and Reactivity of 5-Chloro-2,4-Dihydrosypyridine", x Recl. Tray. Chim. Pays-Bas; 285 (1953).

Lancet J.E., J.D. Rosenblatt, J.E. Karp. (2003) "Farnesyltransferase inhibitors and myeloid malignancies: phase I evidence of Zarnestra activity in high-risk leukemias." Semin Hematol. 39(3 Suppl 2):31-5.

Levis, M. et al. 2001, "A FLT3 tyrosine kinase inhibitor is selectively cytoxic to acute myeloid leukemia blasts harboring FLT3 internal tandem duplication mutations", Blood 98(3):885-7.

Levis, M. et al., "Novel FLT3 tyrosine kinase inhibitors" Expert Opin. Investing. Drugs (2003) 12 (12) 1951-1962.

Levis, M. et al., "Small Molecule FLT3 Tyrosine Kinase Inhibitors" Current Pharmaceutical Design, 2004, 10, 1183-1193.

Levis, M., et al. (2004) "In vitro studies of a FLT3 inhibitor combined with chemotherapy: sequence of administration is important to achieve synergistic cytotoxic effects." Blood. 104(4):1145-50.

Nunez G, Benedict MA, Hu Y, Inohara N. (1998) "Caspases: the proteases of the apoptotic pathway." Oncogene 17:3237-45.

O'Farrell, A.M. et al. "SU11248 is a novel FLT3 tyrosine kinase inhibitor with potent activity in vitro and in vivo" Blood, May 2003; 101:3597-3605.

Olah, G.A. et al., "Formylating Agents", Chemical Reviews, vol. 87, No. 4, 1987.

Prendergast et al., (2001) "Farnesyl Transferase Inhibitors: Mechanism and Applications" Expert Opin Investig Drugs. 10(12):2105-16).

Protecting Groups, P, Kocienski Thieme Medical Publishers, 2000.

Lewis, et al. "Diacetoxypiperidinium Analogs of Acetylcholine", Junal of Medicinal Chemistry, 1973, vol. 16, No. 2 pp. 156-159.

Loader, C., et al., "Pyrrole chemistry. XXIII. The cyanation of substituted pyrroles with chlorosulfonyl isocyanate (CSI). New syntheses of pyrrole-3-carbonitriles.", Can. J. Chem, 59, 2673 (1981).

Pure Appl. Chem., 1976, 45:13-30.

Lovborg H, Gullbo J, Larsson R. (2005) "Screening for apoptosis-classical and emerging techniques." Anticancer Drugs 16:593-9.

Lyon R. , et al., "Synthesis and Evaluation of Phenyl- and Benzoylpiperazines as Potential Serotonergic Agents", J. Med. Chem., 29: 630-4 (1986).

Major, R., et al. "1-Alkoxy-4-phenyl-4-propionoxypiperdines and Their 3-Methyl Homologs as New Analgesics", vol. 26, pp. 1867-1847, (1961).

McKenna, H.J. et al., "Mice lacking flt3 ligand having deficient hematopoiesis affecting hematopoietic progenitor cells, dendritic cells and natural killer cells", Blood Jun. 2000; 95:3489-3497.

Miyaura, N. et al., "Palladium-Catalyzed Cross-Coupling Reactions of Organoboron Compounds", Chem. Rev. 95:2457 (1995).

Modern Amination Methods: Ricci, A., Ed., Wiley-VCH: Weinheim, 2000.

Muci, et al., "Practical Palladium Catalysts for C-N and C-O Bond Formation", Top. Curr., Chem. 219-131-209 (2001.

Murata, K. et al., "Selective cytotoxic mechanism of GTP-14564, a novel tyrosine kinase inhibitor in leukemia cells expressing a constitutively active Fms-like tyrosine kinase 3 (FLT3)" J Biol Chem. Aug. 29, 2003; 278(35):32892-8.

Murata, K. et al., "Synthesis of Alkenylboronates via Palladium-Catalyzed Borylation of Alkenyl Triflates (or lodindes) with Pinacolborane" Synthesis, 2000, No. 6, pp. 778-780.

Nicolai, E., et al., "New Process for the Synthesis of Imidazo[4-5-b] pyridine Derivatives as Potent Orally Active Thromboxane $A_2$ Receptor Antagonists", J. Heterocyclic Chemistry, 31, (73) (1994).

Quentmeier H, et al. FLT3 mutations in acute myeloid leukemia cell lines. Leukemia. Jan. 2003;17:120-124.

Romeo, G., et al, "New Pyrimido [5,4-b_indoles as Ligands for *1-Adrenoceptor Subtypes", J. Med. Chem., 46: 2877-2894 (2003).

Sadick, M. et al., Analysis of Heregulin-Induced ErbB2 Phosphorylation with a High-Throughput Kinase Receptor Activation Enzyme-Linked Immunsorbent Assay, Analytical Biochemistry. 1996; 235:207-214.

Scheijen, B. et al. (2002), "Tyrosine kinase oncogenes innormal hematopoiesis and hematological disease", Oncogene 21(21):3314-33.

Shih L. Y. et al., (2004) "Internal tandem duplication of fms-like tyrosine kinase 3 is associated with poor outcome in patients with myelodysplastic syndrome." Cancer, 101; 989-98.

Simpson WG, The calcium channel blocker verapamil and cancer chemotherapy. Cell Calcium. Dec. 1985;6(6):449-67.

Smith, B. D. et al., "Single-agent CEP-701, a novel FLT3 inhibitor, shows biologic and clinical activity in patients with relapsed or refractory acute myeloid leukemia" Blood, May 2004; 103:3669-3676.

Smith P, "The Curtius Reaction", Organic Reactions 3:337 (1947).

Stirewalt, D.L. et al. (2003), "The role of FLT3 in haematopoietic malignancies", NatRev Cancer 3(9):650-65.

Stone, R.M. et al. "PKC 412 FLT3 inhibitor therapy in AML: results of a phase II trial" an Hematol 2004; 83 Suppl 1:S89-90.

Suzuki, A., "Metal-Catalyzed Coupling Reactions" F. Deiderich, P. Stang, Eds., Wiley-VCH, Weinheim (1998).

Takada, Y., et al. (2004). "Protein farnesyltransferase inhibitor (SCH 66336) abolishes NF-kappaB activation induced by various carcinogens and inflammatory stimuli leading to suppression of NF-kappaB-regulated gene expression and up-regulation of apoptosis."J Biol Chem 279, 26287-99.

Thalhammer et al. Duration of second complete remission in patients with acute myeloid leukemia treated with chemotherapy: a retrospective single-center study. Ann. Hematology, 1996, 72: 216-222.

(56) References Cited

OTHER PUBLICATIONS

Thompson et al., Journal of Industrial and Engineering Chemistry (Washington, D.C.) (1952), 44,1659-62.
Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985).
Tse, K.F. et al., "Inhibition of FLT3-mediated transformation by use of a tyrosine kinase inhibitor" Leukemia, Jul. 15, 2001(7):1001-10.
van Engeland M., L.J. Nieland ,et al. (1998) "Annexin V-affinity assay: a review on an apoptosis detection system based on phosphatidylserine exposure." Cytometry. 31(1):1-9.
Walker et al (Dermatol 212:70-72, 2006; (Abstract Only).
Wustrow, et al, "Coupling of Arylboronic Acids with a Partially Reduced Pyridine Derivative" Synthesis, 993 (1991).
www.cancer.org (accessed online Mar. 2, 2010), "Can Acute Myeloid Luchemia (AML) Be Prevented?".
Yee et al. Synergistic effect of SU11248 with cytarabine or daunorubicin on FLT3 ITD-positive leukemic cells. Blood, 2004, 104: 4202-4209. Published online Aug. 10, 2004.
Yee, K.W.H. et al., "SU5416 and SU5614 inhibit kinase activity of wild-type and mutant FLT3 receptor tyrosine kinase" Blood, Sep. 2002; 100:2941-294.
Zhu et al. Farnesyltransferase inhibitor R115777 (Zarnestra, Tipifarnib) synergizes with paclitaxel to induce apoptosis and mitotic arrest and to inhibit tumor growth of multiple myeloma cells. Blood, vol. 105, No. 12, 4759-4766, Published online Feb. 22, 2005.
Beletskaya et al., *Chem. Rev.*, 100:3009 (2000).
Brase et al., *Angew. Chemie Int. Ed.*, 44(33), 5188-5240, (2005).
Brase et al., Metal-Catalyzed Cross-Coupling Reactions (2nd Edition), p. 217-315, A. de Meijere, F. Diederich, Eds., Wiley-VCH, Weinheim (2004).
Corey et al., *Tetrahedron Lett.*, 29, 995 (1988).
Couturier et al., *Organic Process Research & Development*, 2002, 6, 42-48.
Dirlam et al., *J. Heterocyclic Chem*, 17, 409, (1980).
Dolan, S., et al, *J. Chem., Soc., Chem. Commun.*, 1588-9 (1985).
Fohlisch et al, *Liebigs Annalen der Chemie*, (1), 1-5 (1987) [English Abstract provided].
Galemmo et al., *J. Med. Chem.*, 33(10), 2828-41; (1990).
Guanti et al., *Tetrahedron*, 46 (20), 7081, (1990).
Guanti et al., *Tetrahedron: Asymmetry* 8(13), 2175-2187, (1997).
Hayakawa et al., *Bioorg. Med. Chem. Lett.*, 14(2): 455-8 (2004).
Itsuno et al., Synthesis, 12, 995-6, (1988).
Koutek, et al, Synth. Commun., 6 (4), 305-8 (1976).
Leonard et al., J. Org. Chem., 28, 3021, (1963).
Liu et al., J. Am. Chem. Soc. 2004, 126, 5182.
Martinez_Teipel et al., QSAR & Combinatorial Science, 23(10), 854-858 (2004).
Mock et al., J. Phys. Org. Chem., 16(3), 175-182 (2003).
Myles et al., J. Org. Chem., 55, 1636 (1990).
Nguyen et al., Tetrahedron, 62(4), 647-651; (2006).
Nose et al., Chem. Pharm. Bull., 38(8), 2097-101, (1990).
Quintard et al., J. Org. Chem., 48: 1559-60 (1983).
Reed et al., Synthetic Communications, 20(4), 563-71, (1990).
Roush, W., J. Am. Chem. Soc. 102, 1390 (1980).
Tohma et al., Adv. Syn. Catalysis, 346, 111-124 (2004).
Wustrow et al., Tetrahedron Lett., 35, 61-4 (1994).
Suzuki, A. *In Metal-Catalyzed Cross Coupling Reactions*; Diederich, F., Stang, P. J., Eds.; Wiley-VCH: Weinheim, Germany, 1998; Chapter 2, pp. 49-89.
Chemcats RN 93730-20-2, Nov. 28, 1988.
Chemcats RN 443895-82-7 Apr. 24, 2003.
Chemcats RN 701272-70-0, Jan. 1, 2004.
Chemcats RN 712290-43, Jan. 1, 2004.
Jonas, Nilsson W. et al., "Solid-Phase Synthesis of Libraries Generated from a 4-Phenyl-2-carboxy-piperazine Scaffold", J. Comb. Chem., 2001, 3, 546-553.
Moffett, Robert Bruce et al., "Antiulcer Agents. p-Aminobenzamido Aromatic Compounds", Journal of Medicinal Chemistry, 1971, vol. 14, No. 10, pp. 963-968.
Nilsson et al., J. Comb. Chem., vol. 3, pp. 546-553 (2001).
Rastelli et al. J. Med. Chem., 2003, 46, 2834-2845.
McOmie, J. F. W., "Protecting Groups in Organic Chemistry", 1973.
Albaneze-Walker, J., et al., "Improved Carbonylation of Heterocyclic Chlorides and Electronically Challenging Aryl Bromides", Organic Letters, vol. 6, No. 13, pp. 2097-2100 (2004).
Barnard, C., "Carabonylation of Aryl Halides Extending the Scope of the Reaction", Organic Process Research & Development, vol. 12, pp. 566-574 (2008).
Wall, M., et al., "Cyano-Substituted 2-Carboxylimidazoles: Synthsis of 4-Cyano-1-{{2-tri-methylsily)]methyl}-1H-imiddazole-2-carboxylate Potassium Salt", Synthesis, No. 21, pp. 3377-3379 (2008).
Magnus, P., et al., "Synthesis osf the ABCD-rings of the Insecticidal Indole Alkaloid Nodulisporic Acid", Tetrahedron Letters, vol. 40, pp. 6909-6912 (1999).
Vippagunta, et al., "Crystalline Solids", vol. 48, Advanced Drug Delivery Review, pp. 3-26 (2001).
Wilson, et al., "Reducing Ion Channel Activity in a Series of 4-Heterocyclic Arylamide FMS Inhibitors", Bioorganic & Medicinal Chemical Letters, pp. 3925-3929 (2010).
International Search Report for corresponding Patent Application No. PCT/US2008/080081 dated Mar. 19, 2009.
International Search Report for corresponding Patent Application No. PCT/US2005/037868 dated Sep. 17, 2008.
U.S. Patent Application 07/0249680, filed Oct. 25, 2007 (Illig C., et al.).
U.S. Appl. No. 06/148,812, filed Jul. 6, 2006 (Illig, C., et al.).

\* cited by examiner

PROCESS FOR THE PREPARATION OF HETEROCYCLIC ESTER DERIVATIVES

RELATED APPLICATIONS

This application claims the benefit of U.S. Provisional Patent Application 61/680,412, filed Aug. 7, 2012, which is hereby incorporated by reference in its entirety.

FIELD OF THE INVENTION

The present invention is directed to a process for the preparation of heterocyclic ester derivatives, useful as intermediates in the synthesis of derivatives useful as protein tyrosine kinase inhibitors, more particularly inhibitors of c-fms kinase.

BACKGROUND OF THE INVENTION

Illig, C., et al., in US Patent Publication US2009 0105296 A1, published Apr. 23, 2009 disclose c-FMS kinase inhibitors, derivatives of the following structural formula

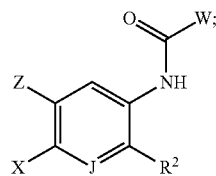

pharmaceutically acceptable salts thereof; and a process for their preparation. Illig, C., et al., in Scheme 1 teach preparation of the derivatives of the above structural formula comprising reacting a compound of formula 1-5

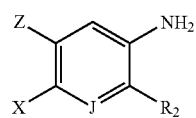

with "a heterocyclic acid $P^1$-WCOOH (or a corresponding salt thereof $P^1$-WCOOM$^2$, where M$^2$ is Li, Na or K) where $P^1$ is an optional protecting group (for example 2-(trimethylsilyl)ethoxymethyl (SEM) such as when W is imidazole, triazole, pyrrole, or benzimidazole) or where $P^1$ is not present such as when W is furan . . . . The coupling can be carried out according to standard procedures for amide bond formation (see for example, M. Bodansky and A. Bodansky, The Practice of Peptide Synthesis, Springer-Verlag, NY (1984)) or by reaction with acid chlorides $P^1$-WCOCl or activated esters $P^1$-WCO$_2$R$^q$ (where R$^q$ is a leaving group such as pentafluorophenyl or N-succinimide)".

Illig, C., et al., in Scheme 9, further teach a process for the preparation of protected carboxylic acids of the formula $P^1$-WCOOH or the corresponding salts of the formula $P^1$-WCOOM$^2$, more particularly for compounds wherein W is imidazolyl. In the process taught by Illig, C., et al., an optionally substituted imidazolyl is protected at the 1-position nitrogen, with a suitably selected protecting group such as MOM or SEM, according to known methods.

The protected imidazole is then "halogenated with a suitable reagent such as N-bromosuccinimide or N-iodosuccinimide under either electrophilic conditions in a solvent such as DCM or CH$_3$CN or under radical conditions in the presence of an initiator such as azobis(isobutyronitrile) (AIBN) in a solvent such as CCl$_4$" to yield the corresponding compound, wherein the 2-position on the imidazole is substituted with the corresponding halogen atom. "Halogen-magnesium exchange on" said compounds yields "the corresponding organomagnesium species, which is then reacted with a suitable electrophile", to yield the corresponding protected ester. Alternatively, the protected imidazole is "deprotonated with a suitable base such as an alkyllithium followed by reaction with an electrophile", to similarly yield the corresponding protected carboxylic acid of formula ester.

The protected ester can then be "hydrolyzed to" the corresponding "carboxylic acids" of formula $P^1$-WCOOH "or carboxylate salts" of formula $P^1$-WCOOM$^2$ (wherein "M$^2$ is Li, Na, or K,) using an aqueous metal hydroxide (MOH) solution, in a suitable solvent."

WALL., M. J., et al., "Cyano-Substituted 2-Carboxylimidazoles: Synthesis of 4-Cyano-1-{[2-(trimethylsilyl)ethoxy]methyl}-1H-imidazole-2-carboxylate Potassium Salt", *Synthesis*, 2008, pp 3377-3379, No. 21 describe the synthesis of 4-cyano-1-{[2-(trimethylsilyl)ethoxy]methyl}-1H-imidazole-2-carboxylate potassium salt where the carboxylate group is introduced via bromine-magnesium exchange on a SEM-protected cyanoimidazole followed by reaction with ethyl cyanoformate. The synthesis includes the equilibration of a regioisomeric mixture of SEM-protected imidazoles to give a single product. The process described by Wall et al. utilizes low temperatures and expensive reagents, which are not preferred for large scale process manufacture.

BARNARD, C. F. J., "Carbonylation of Aryl Halides: Extending the Scope of the Reaction", *Org. Proc. Res. Dev.*, 2008, pp. 566-574, Vol. 12, describes the carbonylation of aryl halides. Barnard et al., describes conditions of carbonylation which use of an inorganic base and temperature greater than 100° C., which are not preferred for large scale manufacture.

ALBANEZE-WALKER, J., et al., "Improved Carbonylation of Heterocyclic Chlorides and Electronically Challenging Aryl Bromides", *Org. Lett.* 2004, pp 2097-2100, Vol. 6, No. 13, describe carbonylation of heterocyclic halides. The process described by Albenese-Walker et al. also use a reaction temperature of 100° C., which is not preferred for large scale manufacture.

There remains however, a need for a process for the preparation of compounds of formula (I), as herein described; wherein the process is suitable for large scale manufacture.

SUMMARY OF THE INVENTION

The present invention is directed to a process for the preparation of compounds of formula (I)

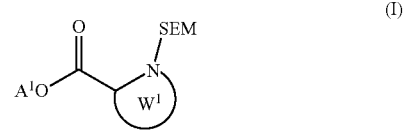

wherein
A¹ is selected from the group consisting of $C_{1-3}$alkyl;
wherein

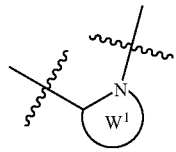

is selected from the group consisting of

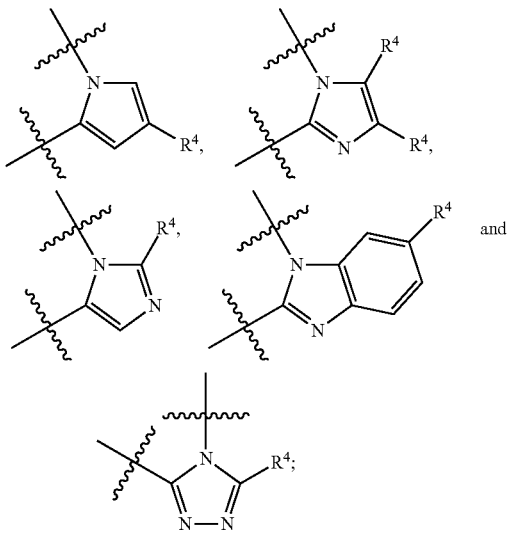

wherein each $R^4$ is independently selected from the group consisting of H, F, Cl, Br, I, —OH, —OCH₃, —OCH₂CH₃, —SC$_{(1-4)}$alkyl, —SOC$_{(1-4)}$alkyl, —SO₂C$_{(1-4)}$alkyl, —C$_{(1-3)}$alkyl, —CO₂R$^d$, —CONR$^e$R$^f$, —CCR$^g$, and —CN;

and wherein R$^d$ is selected from the group consisting of hydrogen and —C$_{(1-3)}$alkyl; R$^e$ is selected from the group consisting of H and —C$_{(1-3)}$alkyl; R$^f$ is selected from the group consisting of H and —C$_{(1-3)}$alkyl; and R$^g$ is selected from the group consisting of H, —CH₂OH and —CH₂CH₂OH;

and pharmaceutically acceptable salts thereof; comprising

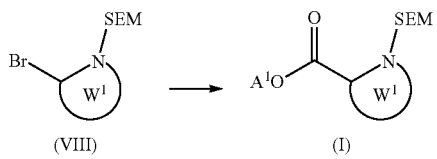

reacting a compound of formula (VIII) or mixture of corresponding SEM-protected resioisomers thereof, with carbon monoxide gas or source of carbon monoxide; in the presence of a tertiary organic base; in the presence of coupling system; in an alcohol of the formula A¹OH; at a temperature in the range of from about 60° C. to about 120° C.; to yield the corresponding compound of formula (I).

In an embodiment, the present invention is directed to a process for the preparation of compounds of formula (I)

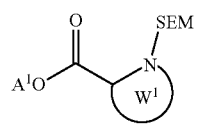

wherein
A¹ is selected from the group consisting of $C_{1-3}$alkyl;
wherein

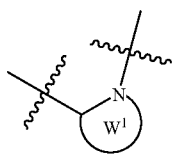

is selected from the group consisting of

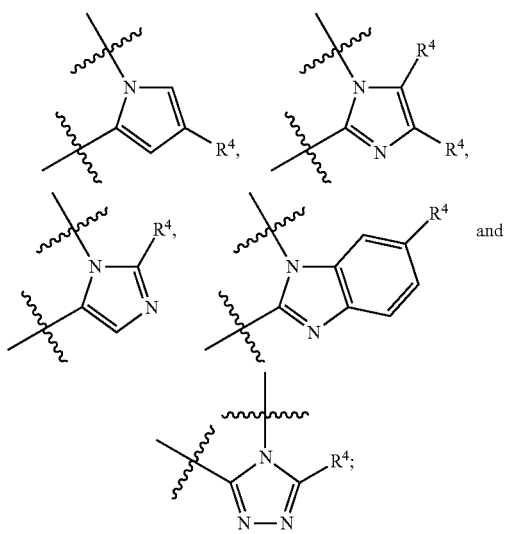

wherein each $R^4$ is independently selected from the group consisting of H, F, Cl, Br, I, —OH, —OCH₃, —OCH₂CH₃, —SC$_{(1-4)}$alkyl, —SOC$_{(1-4)}$alkyl, —SO₂C$_{(1-4)}$alkyl, —C$_{(1-3)}$alkyl, —CO₂R$^d$, —CONR$^e$R$^f$, —CCR$^g$, and —CN; and wherein R$^d$ is selected from the group consisting of hydrogen and —C$_{(1-3)}$alkyl; R$^e$ is selected from the group consisting of H and —C$_{(1-3)}$alkyl; R$^f$ is selected from the group consisting of H and —C$_{(1-3)}$alkyl; and R$^g$ is selected from the group consisting of H, —CH₂OH and —CH₂CH₂OH;

and pharmaceutically acceptable salts thereof; comprising

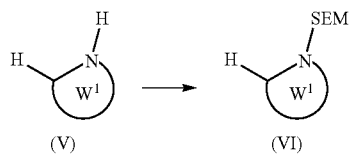

reacting a compound of formula (V) with SEMCl; in the presence of an organic or inorganic base; in an organic solvent; to yield the corresponding compound of formula (VI) or mixture of corresponding SEM-protected regioisomers thereof;

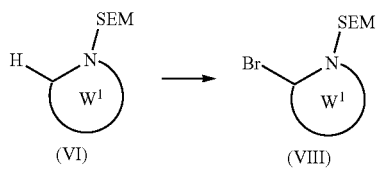

(VI)  (VIII)

reacting the compound of formula (VI) or mixture of corresponding SEM-protected regioisomers thereof with a source of bromine; in an organic solvent; to yield the corresponding compound of formula (VIII) or mixture of corresponding SEM-protected regioisomers thereof;

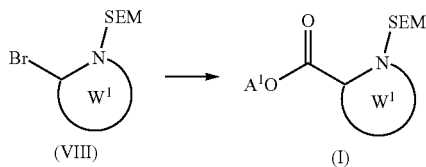

(VIII)  (I)

reacting the compound of formula (VIII) or mixture of corresponding SEM-protected regioisomers thereof with carbon monoxide gas or source of carbon monoxide; in the presence of a tertiary organic base; in the presence of coupling system; in an alcohol of the formula $A^1OH$; at a temperature in the range of from about 60° C. to about 120° C.; to yield the corresponding compound of formula (I).

In an embodiment, the present invention is directed to a process for the preparation of a compound of formula (I-S)

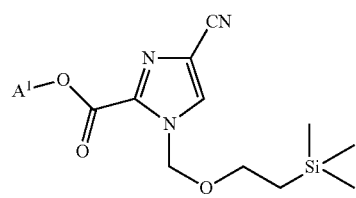

(I-S)

$A^1$ is selected from the group consisting of $C_{1-3}$alkyl; and pharmaceutically acceptable salts thereof; comprising

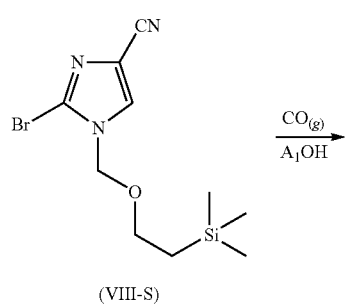

(VIII-S)

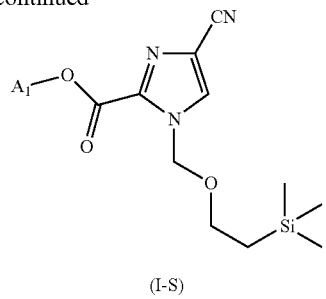

(I-S)

reacting a compound of formula (VIII-S) with carbon monoxide gas or source of carbon monoxide; in the presence of a tertiary organic base; in the presence of a coupling system; in an alcohol of the formula $A^1OH$; at a temperature in the range of from about 60° C. to about 120° C.; to yield the corresponding compound of formula (I-S).

In another embodiment, the present invention is directed to a process for the preparation of a compound of formula (I-S)

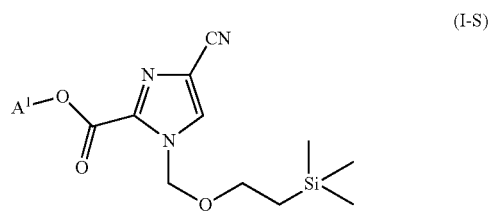

(I-S)

$A^1$ is selected from the group consisting of $C_{1-3}$alkyl; and pharmaceutically acceptable salts thereof; comprising

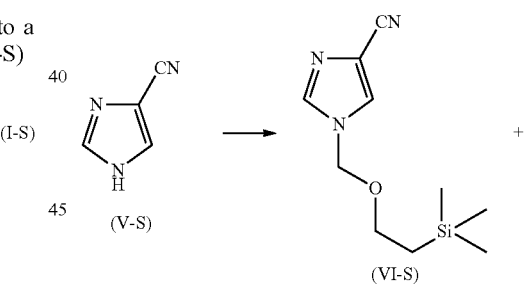

(V-S)  (VI-S)  +

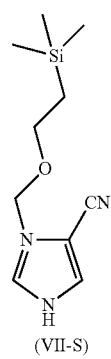

(VII-S)

reacting a compound of formula (V-S) with SEMCl; in the presence of an organic or inorganic base; in an organic solvent; to yield a mixture of the corresponding compound of formula (VI-S) and the corresponding compound of formula (VII-S);

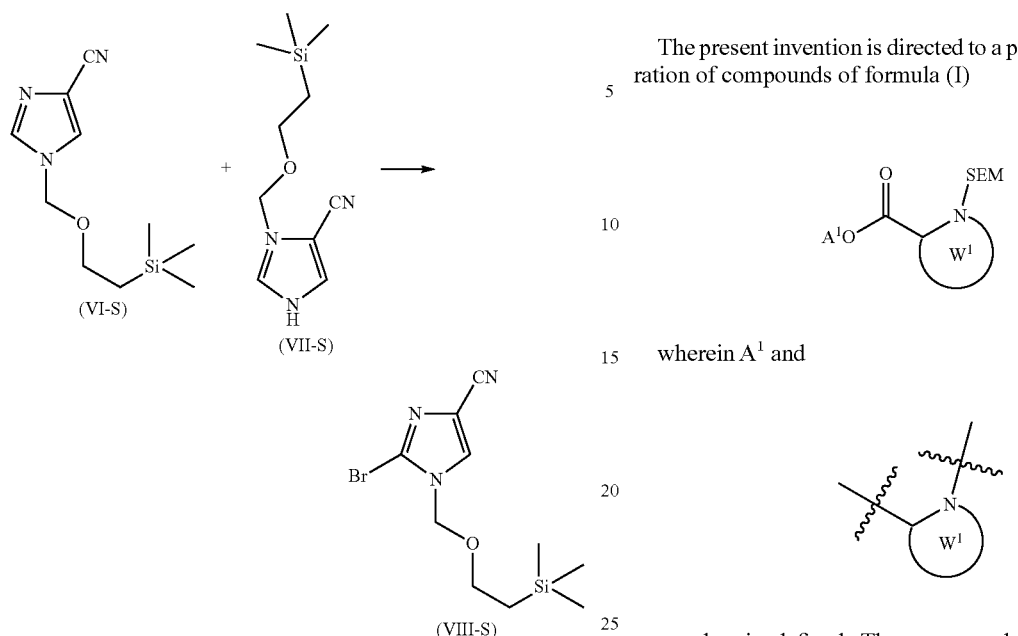

reacting the mixture of the compound of formula (VI-S) and the compound of formula (VII-S) with a source of bromine; in an organic solvent; to yield the corresponding compound of formula (VIII-S);

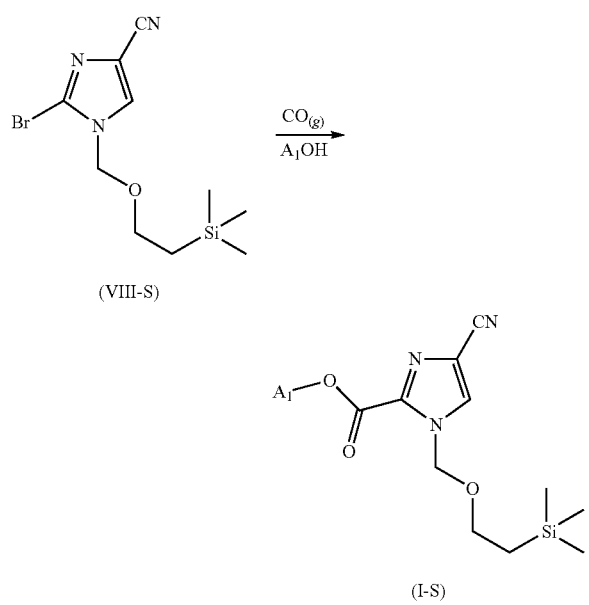

reacting the compound of formula (VIII-S) with carbon monoxide gas or source of carbon monoxide; in the presence of a tertiary organic base; in the presence of a coupling system; in an alcohol of the formula $A^1OH$; at a temperature in the range of from about 60° C. to about 120° C.; to yield the corresponding compound of formula (I-S).

The present invention is further directed to a product prepared according to any of the processes described herein.

DETAILED DESCRIPTION OF THE INVENTION

The present invention is directed to a process for the preparation of compounds of formula (I)

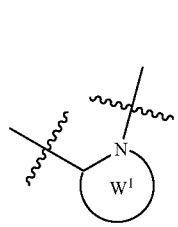 [SMILES: *CN*]
(I)

wherein $A^1$ and

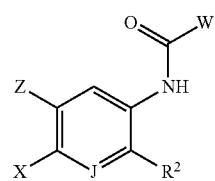

are as herein defined. The compounds of formula (I) are useful as intermediates in the synthesis of, for example, inhibitors of c-fms kinase of the following structural formula as disclosed in ILLIG, C., et al., US Patent Publication 2009/0105296 A1, published Apr. 23, 2009.

In an embodiment, the present invention is directed to a process for the preparation of compounds of formula (I) wherein $A^1$ is selected from the group consisting of methyl, ethyl and isopropyl. In another embodiment, the present invention is directed to a process for the preparation of compounds of formula (I) wherein $A^1$ is selected from the group consisting of methyl and ethyl. In another embodiment, the present invention is directed to a process for the preparation of compounds of formula (I) wherein $A^1$ is methyl. In another embodiment, the present invention is directed to a process for the preparation of compounds of formula (I) wherein $A^1$ is ethyl.

In an embodiment, the present invention is directed to a process for the preparation of compounds of formula (I) wherein

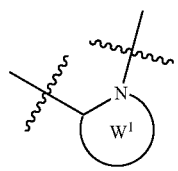 [SMILES: *CN*]

is selected from the group consisting of

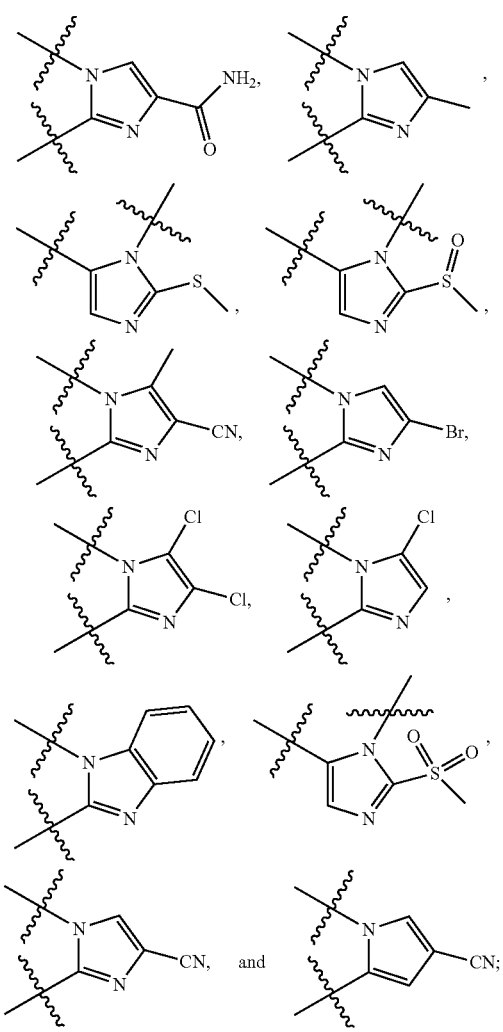

and mixtures of the corresponding SEM-protected regioisomers thereof.

In another embodiment, the present invention is directed to a process for the preparation of compounds of formula (I) wherein

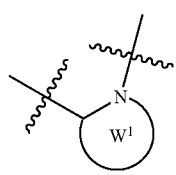 [SMILES: *CN*]

is selected from the group consisting of

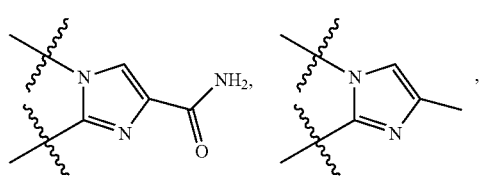

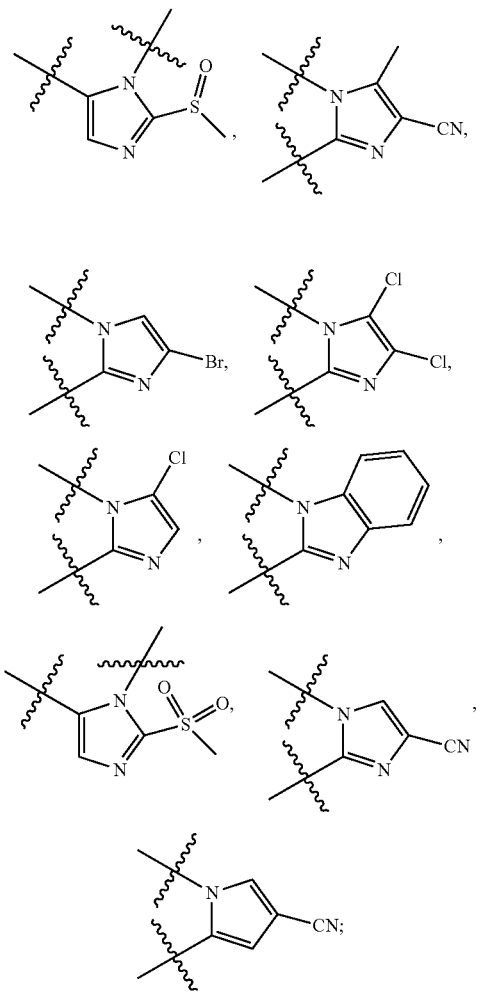

and mixtures of the corresponding SEM-protected regioisomers thereof.

In another embodiment, the present invention is directed to a process for the preparation of compounds of formula (I) wherein

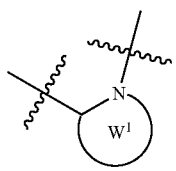 [SMILES: *CN*]

is selected from the group consisting of

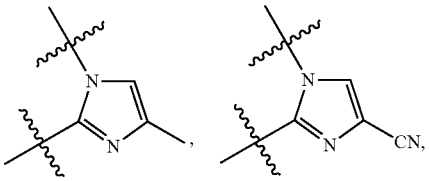

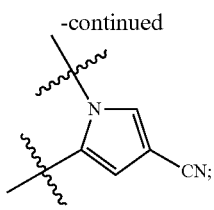

and mixtures of the corresponding SEM-protected regioisomers thereof.

In another embodiment, the present invention is directed to a process for the preparation of compounds of formula (I) wherein

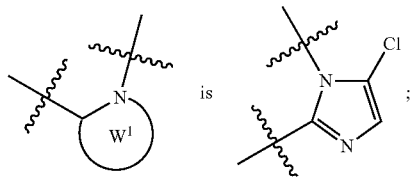

or mixture of the corresponding SEM-protected regioisomers thereof.

In another embodiment, the present invention is directed to a process for the preparation of compounds of formula (I) wherein

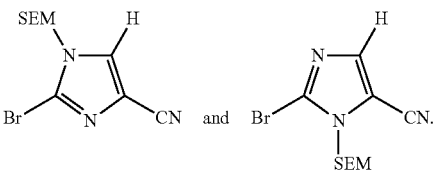

or mixture of the corresponding SEM-protected regioisomers thereof.

As used herein, the term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

As used herein, unless otherwise noted, the term, "mixture of corresponding SEM-protected regioisomers thereof" shall refer to a mixture comprising two or more constitutional isomers; wherein each individual constitutional isomer is defined by the bonding of the SEM-protecting group to one of the nitrogen atom of the $W^1$ ring structure. For example, for the compound of formula (VIII)

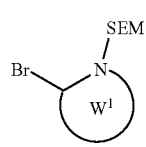

(VIII)

when

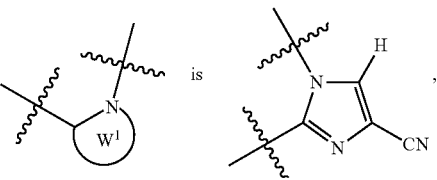

the mixture of corresponding SEM-protected regioisomers thereof shall refer to any mixture of the following two constitutional isomers:

SEM-N imidazole Br-CN and N-SEM imidazole Br-CN.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at a diastereomeric excess of greater than or equal to about 80%, more preferably, at a diastereomeric excess of greater than or equal to about 90%, more preferably still, at a diastereomeric excess of greater than or equal to about 95%, more preferably still, at a diastereomeric excess of greater than or equal to about 98%, most preferably, at a diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

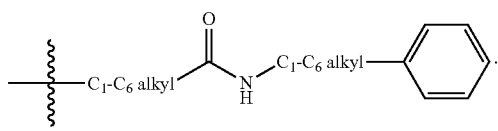

Abbreviations used in the specification, particularly the Schemes and Examples, are as follows
- AIBN=Azobisisobutyronitrile
- BINPA=2,2'-Bis-(diphenylphosphino)-1,1'-binaphthyl
- DCE=Dichloroethane
- DIPEA or DIEA=Diisopropylethylamine
- DMF=N,N-Dimethylformamide
- DMSO=Dimethylsulfoxide
- GC=Gas Chromatography
- MEK=Methyl Ethyl Ketone
- Mesyl=Methylsulfonyl
- MTBE=Methyl tert-Butyl Ether
- NBS=N-Bromosuccinimide
- NORIT A-SUPRA=Powdered activated carbon available from NORIT America Inc.
- $Pd(OAc)_2$=Palladium(II)acetate
- $(Ph_3P)PdCl_2$ or =Bis(triphenylphosphine)palladium (II) $Pd(PPh_3)_2Cl_2$ chloride
- Ph=Phenyl
- SEM=2-(Trimethylsilyl)ethoxymethyl
- SEMCl or SEM-Cl=2-(Trimethylsilyl)ethoxymethyl chloride
- TEA=Triethylamine
- THF=Tetrahydrofuran
- Tosyl=p-Toluenesulfonyl
- XantPhos=4,5-Bis(diphenylphosphino)-9,9-dimethylxanthene As used herein, unless otherwise noted, the term "isolated form" shall mean that the compound is present in a form which is separate from any solid mixture with another compound(s), solvent system or biological environment. In an embodiment, the present invention is directed to a process for the preparation of a compound of formula (I), wherein the compound of formula (I) is prepared in an isolated form. In another embodiment, the present invention is directed to a process for the preparation of a compound of formula (I-S), wherein the compound of formula (I-S) is prepared in an isolated form. In another embodiment, the present invention is directed to a product prepared according to any of the processes as described herein, wherein the product is prepared in an isolated form.

As used herein, unless otherwise noted, the term "substantially pure form" shall mean that the mole percent of impurities in the isolated compound is less than about 5.0 mole percent, preferably less than about 2.0 mole percent, more preferably, less than about 0.5 mole percent, most preferably, less than about 0.1 mole percent. In an embodiment, the present invention is directed to a process for the preparation of a compound of formula (I), wherein the compound of formula (I) is prepared as a substantially pure form. In another embodiment, the present invention is directed to a process for the preparation of a compound of formula (I-S), wherein the compound of formula (I-S) is prepared as a substantially pure form. In another embodiment, the present invention is directed to a product prepared according to any of the processes as described herein, wherein the product is prepared as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5.0 mole percent, preferably less than about 2.0 mole percent, more preferably, less than about 0.5 mole percent, most preferably less than about 0.1 mole percent. In an embodiment, the present invention is directed to a process for the preparation of a compound of formula (I), wherein the compound of formula (I) is prepared in a form which is substantially free of corresponding salt form(s). In an embodiment, the present invention is directed to a process for the preparation of a compound of formula (I-S), wherein the compound of formula (I-S) is prepared in a form which is substantially free of corresponding salt form(s). In another embodiment, the present invention is directed to a product prepared according to any of the processes as described herein, wherein the product is prepared in a form which is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same or different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including, but not limited to, approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter. One skilled in the art will further recognize that wherein a reaction step of the present invention may be carried out in a variety of solvents or solvent systems, said reaction step may also be carried out in a mixture of the suitable solvents or solvent systems.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group, which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows:

$$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee = ([\alpha\text{-obs}]/[\alpha\text{-max}]) \times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs*, ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Processes of the Present Invention

The present invention is directed to a process for the preparation of compounds of formula (I), wherein

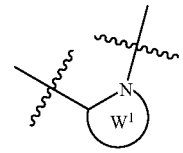

is selected from the group consisting of

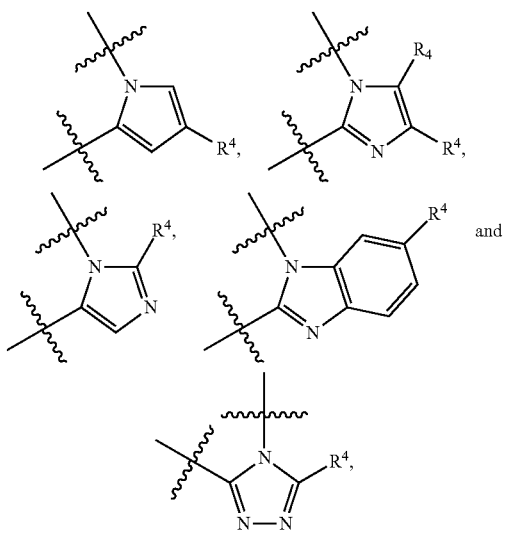

as outlined in Scheme 1, below.

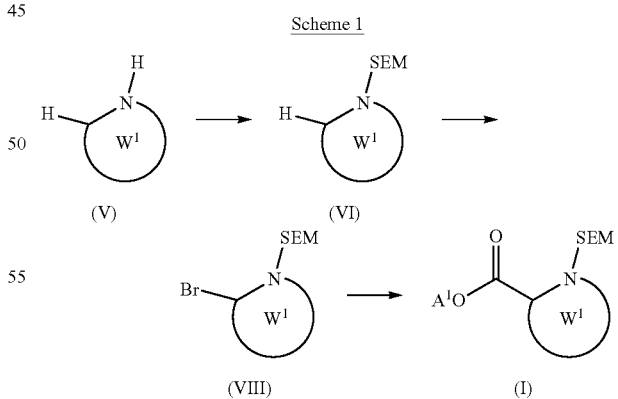

Accordingly, a suitably substituted compound formula (V), a known compound or compound prepared by known methods, is reacted with SEMCl, a known compound, wherein the SEMCl is preferably present in an amount in the range of from about 0.75 to about 2.0 molar equivalents (relative to the moles of the compound of formula (V)), more preferably in an amount in the range of from about 1.01 to about 1.5 molar equivalents, more preferably in an amount greater than 1.0 molar equivalents;

in the presence of a suitably selected organic or inorganic base such as $K_2CO_3$, $Na_2CO_3$, TEA, pyridine, and the like, preferably $K_2CO_3$; wherein the inorganic base is, preferably in an amount in the range of from about 1.0 to about 3.0 molar equivalents (relative to the moles of the compound of formula (V)), more preferably in an amount in the range of from about 1.5 to about 2.5, more preferably in an amount of about 2.0 molar equivalents;

in a suitably selected organic solvent such as acetone, 2-butanone, DCE, and the like, preferably acetone; at a temperature in the range of from about room temperature to about 60° C., more preferably at about 45° C.;

to yield the corresponding compound of formula (VI) or a mixture of the corresponding SEM-protected regioisomers of the compound of formula (VI). Preferably, the mixture of SEM-protected regioisomers of formula (VI) are not separated.

One skilled in the art will recognize that when

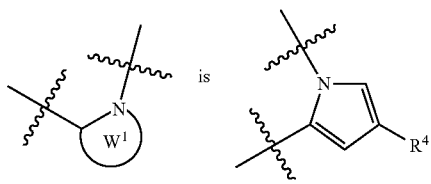

then reacting the compound of formula (V) with SEMCl, as described above, will yield the corresponding SEM-protected compound of formula (VI-R1)

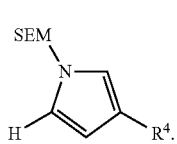

(VI-R1)

One skilled in the art will further recognize that when

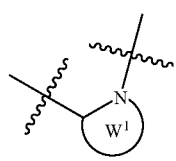

is selected from the group consisting of

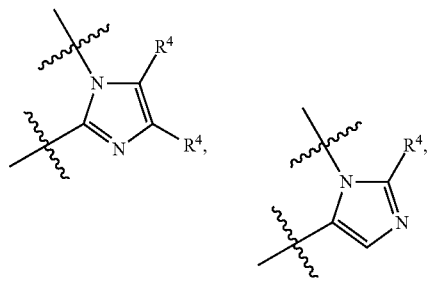

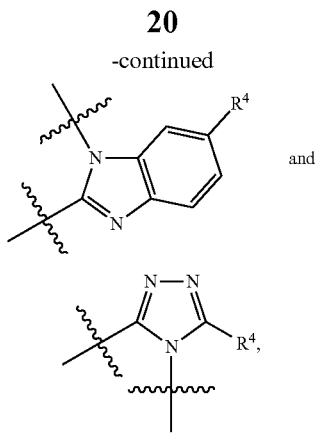

then reacting the compound of formula (V) with SEMCl, as described above, will yield a mixture comprising two or three of the corresponding SEM-protected regioisomers, as defined herein. More particularly, wherein

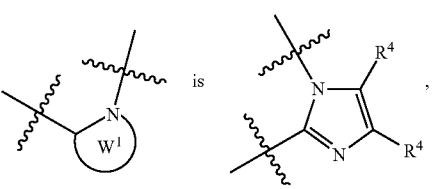

the reaction of the compound of formula (V) with SEMCl may yield a mixture comprising the following two SEM-protected regioisomers:

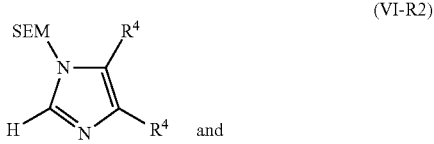

(VI-R2)

(VI-R3)

wherein

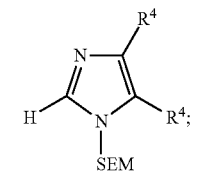

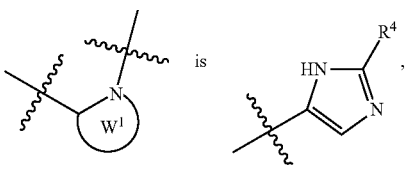

the reaction of the compound of formula (V) with SEMCl may yield a mixture comprising the following two SEM-protected regioisomers:

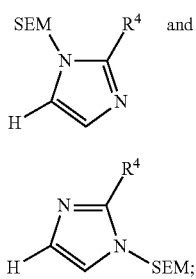
(VI-R4)

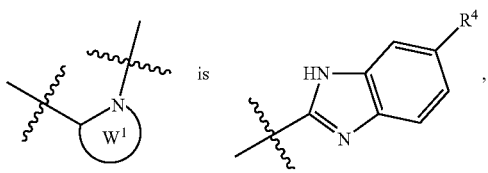
(VI-R5)

wherein

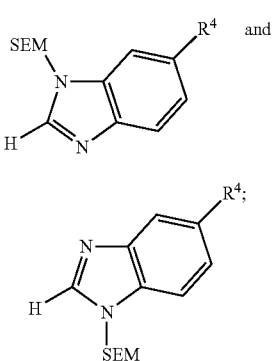

the reaction of the compound of formula (V) with SEMCl may yield a mixture comprising the following two SEM-protected regioisomers:

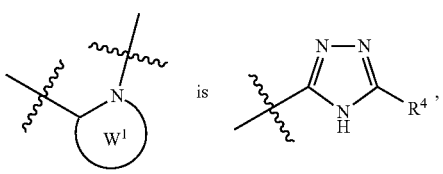
(VI-R6) and (VI-R7);

and wherein

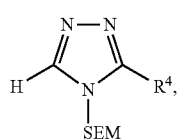

the reaction of the compound of formula (V) with SEMCl may yield a mixture comprising any two or three of the following SEM-protected regioisomers:

(VI-R8)

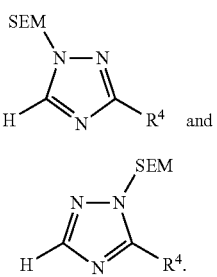
(VI-R9) and (VI-R10)

The compound of formula (VI) or corresponding mixture of regioisomers of the compound of formula (VI) is reacted with a suitably selected source of bromine, such as NBS, $Br_2(g)$, 1,3-dibromo-5,5-dimethyl-hydantoin, and the like, preferably NBS; wherein the source of bromine is preferably present in an amount in the range of from about 1.0 to about 2.0 molar equivalents, more preferably in an amount in the range of from about 1.05 to about 1.5 molar equivalents, more preferably in an amount in the range of from about 1.05 to about 1.2 molar equivalents;

optionally in the presence of a suitably selected initiator such as AIBN, and the like; wherein the initiator is preferably present in a catalytic amount, for example in an amount of about 1.0 mol % (i.e. 0.01 molar equivalents);

in a suitably selected organic solvent such as DCE, $CCl_4$, and the like, preferably DCE; preferably at a temperature in the range of from about 45° C. to about 100° C., more preferably at a temperature in the range of from about 55° C. to about 80° C., more preferably at a temperature at about 60° C.; to yield the corresponding compound of formula (VIII).

The compound of formula (VIII) is reacted with carbon monoxide gas or a suitably selected source of carbon monoxide such as a suitably selected metal carbonyl such as tungsten hexacarbonyl, mollibdinum hexacarbonyl, and the like, optionally under a carbon monoxide atmosphere; wherein the compound of formula (VIII) is preferably reacted with the carbon monoxide gas under an atmosphere of carbon monoxide, preferably at a pressure in the range of from about 40 psi to about 90 psi, more preferably at a pressure of about 60 psi, for example, at a pressure in the range of from about 3.0 bar to about 4.0 bar;

in the presence of a tertiary organic base such as TEA, DIPEA, and the like, preferably TEA; wherein the organic base is preferably present in an amount in the range of from about 1.05 to about 15.0 molar equivalents (relative to the moles of the compound of formula (VIII)), more preferably in an amount in the range of from about 1.05 to about 5 molar equivalents, more preferably in an amount in the range of from about 2.0 to about 4.0 molar equivalents, more preferably in an amount of about 3.0 molar equivalents; (wherein one skilled in the art will recognize that although the use of a non-tertiary amine may yield desired product, the use of a non-tertiary amine will also result in competition during the reaction and therefore lower yields of the desired product);

in the presence of a suitably selected coupling system such as a pre-made catalyst coupling system, such as BINAP-$PdCl_2$, $(Ph_3P)_2PdCl_2$ and the like, or an in situ catalyst coupling system, such as mixtures of a suitably selected palladium compound such as $PdCl_2(CH_3CN)_2$, $Pd(OAc)_2$, and the like and a suitably selected ligand such as BINAP, XantPhos, and the like, preferably a mixture of $Pd(OAc)_2$ and XantPhos; for example, a 1:1 (molar) mixture of a palladium compound and a ligand, preferably a 1:1 (molar) mixture of $Pd(OAc)_2$ and XantPhos;

wherein the coupling system, or each component of the in situ catalyst coupling system, is preferably present in an amount in the range of from about 2.0 mol % to about 6.0 mol % (relative to the moles of the compound of formula (VIII)), more preferably, in an amount in the range of form about 2.0 mol % to about 3.5 mol %, more preferably in an amount of about 2.5 mol %; (wherein the choice of XantPhos results in, for example, improved yields);

(In an example, the coupling system is an in situ mixture of a palladium compound and a ligand, wherein the coupling system is present in an amount of about 5.0 mol %. In another example, the coupling system is an in situ mixture of a palladium compound and a ligand, wherein the palladium compound is present in an amount of about 2.5 mol % and the ligand is present in an amount of about 2.5 mol %.)

in a suitably selected alcohol (solvent) of the formula $A^1OH$, wherein $A^1$ is selected from the group consisting of $C_{1-3}$alkyl, preferably, $A^1$ is selected from the group consisting of methyl and ethyl, more preferably $A^1$ is ethyl; wherein the alcohol of formula $A^1OH$ is preferably present in an amount in the range of from about 1.5 molar to about 5.0 molar, more preferably in an amount in the range of from about 2.0 molar to about 4.0 molar;

preferably at a temperature in the range of from about 60° C. to about 120° C., more preferably at a temperature in the range of from about 70° C. to about 90° C., more preferably at about 80° C.; (wherein the lower temperature results in, for example, less de-SEM by-product formation) to yield the corresponding compound of formula (I).

In an embodiment, the present invention is directed to a process for the preparation of a compound of formula (I-S), as outlined in Scheme 2, below.

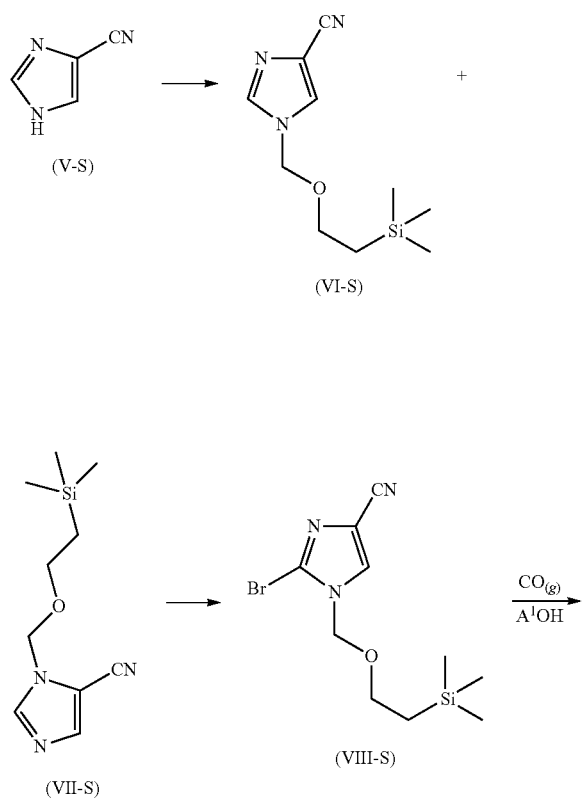

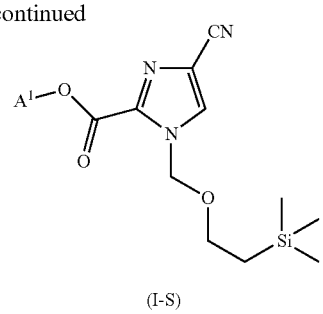

(I-S)

Accordingly, a suitably substituted compound formula (V-S), a known compound or compound prepared by known methods, is reacted with SEMCl, a known compound, wherein the SEMCl is preferably present in an amount in the range of from about 0.75 to about 2.0 molar equivalents (relative to the moles of the compound of formula (V-S)), more preferably in an amount in the range of from about 1.01 to about 1.5 molar equivalents, more preferably in an amount greater than 1.0 molar equivalents;

in the presence of a suitably selected organic or inorganic base such as $K_2CO_3$, $Na_2CO_3$, TEA, pyridine, and the like, preferably $K_2CO_3$; wherein the inorganic base is, preferably in an amount in the range of from about 1.0 to about 3.0 molar equivalents (relative to the moles of the compound of formula (V-S)), more preferably in an amount in the range of from about 1.5 to about 2.5, more preferably in an amount of about 2.0 molar equivalents;

in a suitably selected organic solvent such as acetone, 2-butanone, DCE, and the like, preferably acetone; at a temperature in the range of from about room temperature to about 60° C., more preferably at about 45° C.;

to yield a mixture of regioisomers, the corresponding compound of formula (VI-S) and compound of formula (VII-S). Preferably, the mixture of regioisomers of formula (VI-S) and formula (VII-S) are not separated.

The mixture of regioisomers of formula (VI-S) and formula (VII-S) is reacted with a suitably selected source of bromine, such as NBS, $Br_2(g)$, 1,3-dibromo-5,5-dimethylhydantoin, and the like, preferably NBS; wherein the source of bromine is preferably present in an amount in the range of from about 1.0 to about 2.0 molar equivalents, more preferably in an amount in the range of from about 1.05 to about 1.2.5 molar equivalents, more preferably in an amount in the range of from about 1.05 to about 1.2 molar equivalents;

optionally in the presence of a suitably selected initiator such as AIBN, and the like; wherein the initiator is preferably present in a catalytic amount, for example in an amount of about 1.0 mole percent (0.01 molar equivalents);

in a suitably selected organic solvent such as DCE, $CCl_4$, and the like, preferably DCE; preferably at a temperature in the range of from about 45° C. to about 100° C., more preferably at a temperature in the range of from about 55° C. to about 80° C., more preferably at a temperature at about 60° C.;

to yield the corresponding compound of formula (VIII-S).

The compound of formula (VIII-S) is reacted with carbon monoxide gas (or a suitably selected source of carbon monoxide such as a suitably selected metal carbonyl such as tungsten hexacarbonyl, mollibdinum hexacarbonyl, and the like, optionally under a carbon monoxide atmosphere); wherein the compound of formula (VIII) is preferably reacted with the carbon monoxide gas under an atmosphere of carbon monoxide, preferably at a pressure in the range of from about 40 psi to about 90 psi, more preferably at a pressure of about 60 psi (for example, at a pressure in the range of from about 3.0 bar to about 4.0 bar);

in the presence of a tertiary organic base such as TEA, DIPEA, and the like, preferably TEA; wherein the organic base is preferably present in an amount in the range of from about 1.05 to about 15.0 molar equivalents (relative to the moles of the compound of formula (VIII-S)), more preferably in an amount in the range of from about 1.05 to about 5.0 molar equivalents, more preferably in an amount in the range of from about 2.0 to about 4.0 molar equivalents, more preferably in an amount of about 3.0 molar equivalents; (wherein one skilled in the art will recognize that although the use of a non-tertiary amine may yield desired product, the use of a non-tertiary amine will also result in competition during the reaction and therefore lower yields of the desired product);

in the presence of a suitably selected coupling system such as a pre-made catalyst coupling system, such as BINAP-PdCl$_2$, (Ph$_3$P)$_2$PdCl$_2$ and the like, or an in situ catalyst coupling system, such as mixtures of a suitably selected palladium compound such as PdCl$_2$(CH$_3$CN)$_2$, Pd(OAc)$_2$, and the like and a suitably selected ligand such as BINAP, XantPhos, and the like, preferably a mixture of Pd(OAc)$_2$ and XantPhos; for example, a 1:1 (molar) mixture of a palladium compound and a ligand, preferably a 1:1 (molar) mixture of Pd(OAc)$_2$ and XantPhos;

wherein the coupling system, or each component of the in situ catalyst coupling system, is preferably present in an amount in the range of from about 2.0 mol % to about 6.0 mol % (relative to the moles of the compound of formula (VIII)), more preferably in an amount in the range of form about 2.0 mol % to about 3.5 mol %, more preferably in an amount of about 2.5 mol %; (wherein the choice of XantPhos results in, for example, improved yields);

(In an example, the coupling system is an in situ mixture of a palladium compound and a ligand, wherein the coupling system is present in an amount of about 5.0 mol %. In another example, the coupling system is an in situ mixture of a palladium compound and a ligand, wherein the palladium compound is present in an amount of about 2.5 mol % and the ligand is present in an amount of about 2.5 mol %.)

in a suitably selected alcohol (solvent) of the formula A$^1$OH, wherein A$^1$ is selected from the group consisting of C$_{1-3}$alkyl, preferably, A$^1$ is selected from the group consisting of methyl and ethyl, more preferably, A$^1$ is ethyl; wherein the alcohol of formula A$^1$OH is preferably present in an amount of about 1.5 to about 5.0 molar, more preferably in an amount of 2.0 to about 4.0 molar;

preferably at a temperature in the range of from about 60° C. to about 120° C., more preferably at a temperature in the range of from about 70° C. to about 90° C., more preferably at about 80° C.; (wherein the lower temperature results in, for example, less de-SEM by-product formation); to yield the corresponding compound of formula (I-S).

EXAMPLES

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like. One skilled in the art will further recognize that in the Examples that follow, the term "rag-layer" refers to the emulsion which may form between the organic and aqueous layers during separation work-up.

Synthesis Example 1

Ethyl, 4-cyano-1-((2-(trimethylsilyl)ethoxy)methyl)-1H-imidazole-2-carboxylate

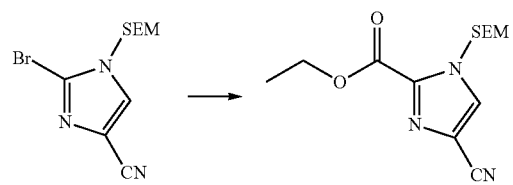

A 60 mL stainless steel MULTIMAX reactor was charged with 2-bromo-1-((2-(trimethylsilyl)ethoxy)methyl)-1H-imidazole-4-carbonitrile (2.41 g, 7.97 mmol, 1 equiv.), ethanol (32.0 mL, 25.32 g, 549.64 mmol) TEA (3.30 mL, 2.40 g, 23.68 mmol), racemic BINAP (0.12 g, 0.20 mmol) and dichlorobis(acetonitrile)palladium (II) (0.05 g, 0.20 mmol). The reactor was closed, flushed with nitrogen three times, heated to 70° C. and pressurized to an internal pressure below 0.5 bar. Carbon monoxide was introduced into the reactor at a pressure of 4 bar, with stirring at 400 rpm. The reaction was allowed to proceed with GC monitoring. After 4 hours at 70° C., the temperature was increased to 80° C., the stirring increased to 600 rmp, while CO pressure was maintained at 4 bar. The reaction was allowed to proceed for an addition 3 days under these conditions. The resulting mixture was then allowed to cool to room temperature resulting in a red solution with black precipitation at the bottom of the reactor. The resulting product mixture was filtered, washed with ethanol and the reactor rinsed with ethanol; for a total volume of 63 mL.

To a portion of the product mixture (25 mL) was added water (15 mL) and the resulting mixture was extracted with isopropylacetate (20 mL). Additional water (15 mL) was added to yield a good separation, with the organic layer washed two more times with water (15 mL). The resulting combined organic layer (a red solution) was allowed to stand overnight, with the mixture solidifying.

The remaining portion (33 mL) of the product mixture was evaporated on a rotovap and the resulting residue dissolved in isopropylacetate (20 mL) and water (20 ml). The resulting layers were separated, the organic layer washed twice with water (20 mL), and the resulting mixture evaporated on a rotovap to yield a red oily residue.

Synthesis Example 2

Ethyl, 4-cyano-1-((2-(trimethylsilyl)ethoxy)methyl)-1H-imidazole-2-carboxylate

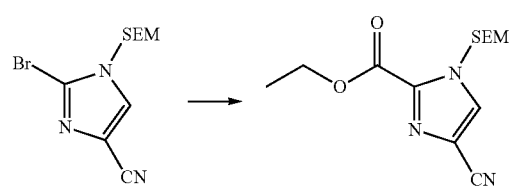 [SMILES: C[Si](C)(C)CCOCn1cc(C#N)nc1Br ; CCOC(=O)c1nc(C#N)cn1COCC[Si](C)(C)C]

A 500 mL stainless steel MULTIMAX reactor was charged with 2-bromo-1-((2-(trimethylsilyl)ethoxy)methyl)-1H-imidazole-4-carbonitrile (25.80 g, 75.12 mmol, 1 equiv.), ethanol (300.00 mL, 237.39 g, 5152.92 mmol) TEA (32.00 mL, 23.23 g, 229.58 mmol), XantPhos (1.10 g, 1.90 mmol) and Pd(OAc)$_2$ (0.41 g, 1.83 mmol). The reactor was closed, flushed with twice with carbon monoxide, heated to 80° C. and pressurized to an internal pressure below 1.0 bar. Carbon monoxide was introduced into the reactor at a pressure of 4 bar, with stirring at 500 rpm. The reaction was allowed to proceed with GC monitoring. After 2 hours, the stirring speed was increased to 750 rpm and the reaction allowed to proceed at these conditions overnight. The resulting mixture was cooled to room temperature, and the resulting mixture (which contained a yellow residue) transferred to a pear-shaped flask. The solvent was evaporated to yield a dry residue.

The dry residue was taken up in toluene (225 mL), water was added (150 mL), the mixture was stirred for a few moments and the rag-layer filtered off. The resulting layers were separated. The organic layer was washed with water (150 mL), the rag-layer discarded with the aqueous layer, and washed a second time with water (150 mL). The organic layer was then transferred to a 4-necked round bottom flask and about 50 mL of solvent was distilled off. The mixture was then azeotropically dried at 100° C., with some material observed to precipitate out and stick to the glass walls of the flask.

To the remainder of the reaction mixture was added silica gel thiol (8 g) and the resulting mixture stirred at 60° C. for a few hours, then held without stirring overnight. The resulting mixture was then filtered. To the resulting mixture was again added silica gel thiol (6 g) and the resulting mixture stirred at 60° C. for 4 hours. The resulting mixture was filtered, the solids washed with toluene and the organic layer evaporated on a rotavap to yield the title compound as a residue.

Crystallization

To the remainder of the residue (17.7 g) was added MTBE (18 mL) and the resulting mixture heated to reflux. A solution was observed to be obtained at 40° C., while at reflux temperature hexane (85 mL) was added. The resulting mixture was cooled to 35° C. and seeded, with immediate precipitation observed. The resulting mixture was then cooled to room temperature, the solids filtered, washed with a mixture of 5:1 hexane:MTBE (60 mL total) and dried for 2 hrs at 45° C. to yield the title compound as a solid Synthesis Example 3

Ethyl, 4-cyano-1-((2-(trimethylsilyl)ethoxy)methyl)-1H-imidazole-2-carboxylate

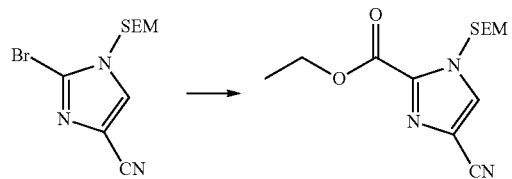 [SMILES: C[Si](C)(C)CCOCn1cc(C#N)nc1Br ; CCOC(=O)c1nc(C#N)cn1COCC[Si](C)(C)C]

A 5 L reactor was charged with 2-bromo-1-((2-(trimethylsilyl)ethoxy)methyl)-1H-imidazole-4-carbonitrile (337.6 g, 1116.96 mmol), ethanol (2.4 L), TEA (472 mL), Pd(OAc)$_2$ (6.32 g, 28.21 mmol) and XantPhos (16.24 g, 28.05 mmol). The reactor was set to stir, flushed 10 times with nitrogen, then with carbon monoxide 3 times at a pressure of about 5 bar. The reactor was then charged with 1.0 bar carbon monoxide and heated to 80° C. The carbon monoxide charge was then increased to about 4-5 bar and the reaction mixture stirred at 900 r/min for 20 hours, then cooled to room temperature.

The solvent was evaporated on a rotovap to yield a red solid residue. To the residue was added toluene (1100 mL) and water (1100 mL) and the mixture stirred for 20 min, then filtered. The solids were washed with toluene (50 mL). The layers of the resulting mixture were separated, the organic layer washed two more times with water (1000 mL). The combined organic layers were azeotropically dried at about 110° C., with about 100 mL of solvent removed.

The resulting mixture was cooled to 90° C. At this temperature 33.4 grams NORIT A-SUPRA (33.4 g) was added and the resulting mixture stirred for two more hours at 90° C. The resulting mixture was then cooled to room temperature, and filtered, with the solids washed twice with toluene (50 mL). The resulting mixture was transferred to a round bottom flask and silica gel thiol (82 g) was added. The resulting mixture was heated to 90° C., and stirred for 4 hours at this temperature. The resulting mixture was then cooled to room temperature, filtered, and the solids washed two times with toluene (50 mL). The resulting mixture again was transferred to a round bottom flask and silica gel thiol (82 g) was added. The resulting mixture was heated to 90° C., and stirred for 20 hours at this temperature. The resulting mixture was then cooled to room temperature, filtered, and the solids washed two times with toluene (50 mL). The resulting mixture again was transferred to a round bottom flask and silica gel thiol (82 g) was added. The resulting mixture was heated to 90° C., and stirred for 4 hours at this temperature. The resulting mixture was then cooled to room temperature, filtered, and the solids washed two times with toluene (50 mL).

The resulting mixture was then evaporated on a rotovap at 50° C. to yield a yellow solid residue. To the residue was then added ethanol +2% MEK (880 mL) and the resulting mixture heated to 4° C., resulting in an orange homogeneous solution. Water (44 mL) was then added. Seeds of the desired product were then added and the resulting mixture stirred at 40° C. for 2 hours. The resulting mixture was allowed to cool to room temperature overnight, then filtered. The solids were washed twice with a mixture of ethanol:water (150 mL:100 mL, 125 mL), then dried overnight at 50° C. to yield the title compound as a solid.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A process for the preparation of a compound of formula

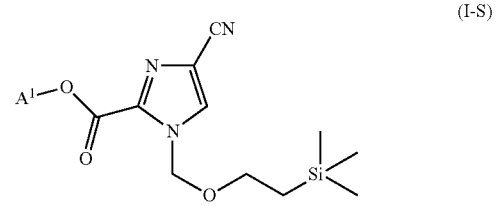

$A^1$ is selected from the group consisting of $C_{1-2}$ alkyl; or a pharmaceutically acceptable salt thereof; comprising

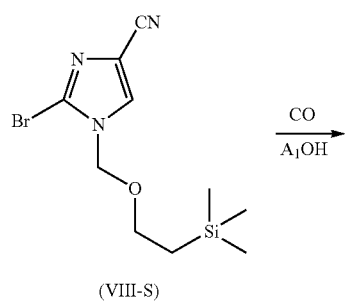

(VIII-S)

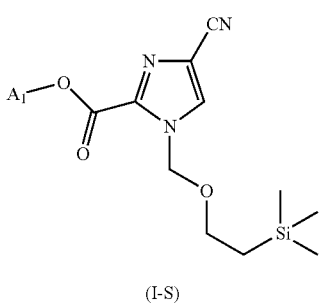

(I-S)

reacting the compound of formula (VIII-S) with carbon monoxide gas, wherein the carbon monoxide gas is present in an amount of about 60 psi; in the presence of a TEA, wherein the TEA is present in an amount of about 3.0 molar equivalents; in the presence of coupling system which is a 1:1 mixture of $Pd(OAc)_2$ and XantPhos; wherein the $Pd(OAc)_2$ is present in an amount of about 2.5 mol %; wherein the XantPhos is present in an amount of about 2.5 mol %; in an alcohol of the formula $A^1OH$ which is methanol or ethanol; at a temperature of about 80° C.

2. A process according to claim 1, wherein the alcohol of formula $A^1OH$ is ethanol.

3. A process according to claim 2, wherein the alcohol of formula $A^1OH$ is present in an amount in the range of from about 1.5 molar to about 5.0 molar.

4. A process according to claim 3, wherein the alcohol of formula $A^1OH$ is present in an amount in the range of from about 2.0 molar to about 4.0 molar.

5. A process according to claim 1, further comprising

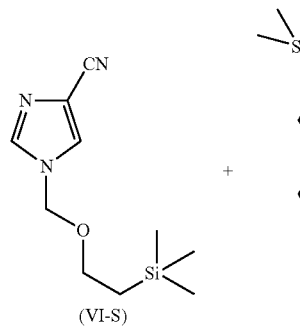 + 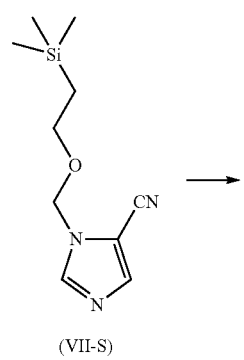 →

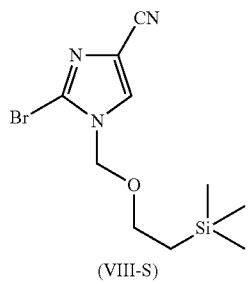

(VIII-S)

reacting a mixture of the compound of formula (VI-S) and the compound of formula (VII-S) with a source of bromine; in an organic solvent; to yield the corresponding compound of formula (VIII-S).

6. A process according to claim 5, further comprising

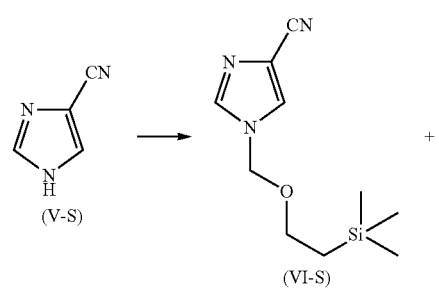 +

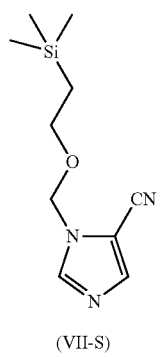

(VII-S)

reacting a compound of formula (V-S) with SEMCl; in the presence of an organic or inorganic base; in an organic solvent; to yield a mixture of the corresponding compound of formula (VI-S) and the corresponding compound of formula (VII-S).

* * * * *